(12) United States Patent
Fadhel et al.

(10) Patent No.: US 11,427,519 B2
(45) Date of Patent: Aug. 30, 2022

(54) ACID MODIFIED RED MUD AS A CATALYST FOR OLEFIN ISOMERIZATION

(71) Applicant: Saudi Arabian Oil Company, Dhahran (SA)

(72) Inventors: Bandar A. Fadhel, Dhahran (SA); Mohammed A. Albuali, Dammam (SA); Munir D. Khokhar, Dhahran (SA); Rami Bamagain, Al Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 84 days.

(21) Appl. No.: 17/140,242

(22) Filed: Jan. 4, 2021

(65) Prior Publication Data

US 2022/0213008 A1  Jul. 7, 2022

(51) Int. Cl.
| | | |
|---|---|---|
| *C07C 5/25* | (2006.01) | |
| *B01J 21/12* | (2006.01) | |
| *B01J 37/03* | (2006.01) | |
| *B01J 21/06* | (2006.01) | |
| *B01J 23/78* | (2006.01) | |
| *B01J 37/08* | (2006.01) | |
| *B01J 6/00* | (2006.01) | |

(Continued)

(52) U.S. Cl.
CPC ............ *C07C 5/2512* (2013.01); *B01J 6/001* (2013.01); *B01J 21/063* (2013.01); *B01J 21/12* (2013.01); *B01J 23/78* (2013.01); *B01J 35/023* (2013.01); *B01J 37/0036* (2013.01); *B01J 37/031* (2013.01); *B01J 37/08* (2013.01); *C07B 63/00* (2013.01); *C07C 2521/06* (2013.01); *C07C 2521/12* (2013.01); *C07C 2523/78* (2013.01)

(58) Field of Classification Search
CPC . B01J 6/001; B01J 21/063; B01J 21/12; B01J 23/78; B01J 35/023; B01J 37/0036; B01J 37/031; B01J 37/08; C07B 63/00; C07C 5/2512; C07C 2521/06; C07C 2521/12; C07C 2523/78

See application file for complete search history.

(56) References Cited

U.S. PATENT DOCUMENTS

| | | |
|---|---|---|
| 106,836 A | 8/1870 | Kuhlmann |
| 665,346 A | 1/1901 | Reed |

(Continued)

FOREIGN PATENT DOCUMENTS

| | | |
|---|---|---|
| CA | 2938299 | 5/2015 |
| CN | 104923234 | 12/2017 |

(Continued)

OTHER PUBLICATIONS

Sushil et al. ("Modification of red mud by acid treatment and its application for CO removal." Journal of Hazardous Materials 203-204 (2012) 264-273) (Year: 2012).*

(Continued)

*Primary Examiner* — In Suk C Bullock
*Assistant Examiner* — Jason Y Chong
(74) *Attorney, Agent, or Firm* — Fish & Richardson P.C.

(57) ABSTRACT

A system and a method for isomerizing a 2-butene feed stream to form a 1-butene product stream are provided. An exemplary method includes calcining the red mud, flowing a butene feedstock over the red mud in an isomerization reactor, and separating 1-butene from a reactor effluent.

14 Claims, 4 Drawing Sheets

(51) Int. Cl.
    *B01J 35/02*     (2006.01)
    *B01J 37/00*     (2006.01)
    *C07B 63/00*     (2006.01)

(56) References Cited

U.S. PATENT DOCUMENTS

| | | |
|---|---|---|
| 701,987 A | 6/1902 | Alz |
| 978,576 A | 12/1910 | Goodell |
| 2,378,905 A | 6/1945 | Bates |
| 2,614,066 A | 10/1952 | Cornell |
| 2,910,426 A | 10/1959 | Gluesenkamp |
| 3,288,692 A | 11/1966 | Leduc |
| 3,409,540 A | 11/1968 | Gould et al. |
| 3,427,235 A | 2/1969 | Leduc |
| 3,527,834 A | 9/1970 | Kehl et al. |
| 3,533,938 A | 10/1970 | Leas |
| 3,585,217 A | 6/1971 | Titzenthaler |
| 3,632,497 A | 1/1972 | Leduc |
| 3,702,292 A | 11/1972 | Burich |
| 3,726,789 A | 4/1973 | Kovach |
| 3,755,143 A | 8/1973 | Hosoi et al. |
| 3,856,659 A | 12/1974 | Owen |
| 3,894,059 A | 7/1975 | Selvaratnam |
| 4,064,062 A | 12/1977 | Yurko |
| 4,090,949 A | 5/1978 | Owen et al. |
| 4,119,507 A | 10/1978 | Simmrock et al. |
| 4,134,824 A | 1/1979 | Kamm et al. |
| 4,230,551 A | 10/1980 | Salyer et al. |
| 4,264,435 A | 4/1981 | Read et al. |
| 4,297,203 A | 10/1981 | Ford et al. |
| 4,310,501 A | 1/1982 | Reh et al. |
| 4,332,663 A | 6/1982 | Berneke |
| 4,426,276 A | 1/1984 | Dean et al. |
| 4,434,031 A | 2/1984 | Horowitz et al. |
| 4,522,802 A | 6/1985 | Setzer et al. |
| 4,527,003 A | 7/1985 | Okamoto et al. |
| 4,560,451 A | 12/1985 | Nielsen |
| 4,587,011 A | 5/1986 | Okamoto et al. |
| 4,602,986 A | 7/1986 | Ellis et al. |
| 4,655,904 A | 4/1987 | Okamoto et al. |
| 4,725,349 A | 2/1988 | Okamoto et al. |
| 4,735,728 A | 4/1988 | Wemhoff |
| 4,761,394 A | 8/1988 | Lauritzen |
| 4,786,400 A | 11/1988 | Farnsworth |
| 4,830,728 A | 5/1989 | Herbst et al. |
| 4,992,160 A | 2/1991 | Long et al. |
| 5,012,360 A | 4/1991 | Yamauchi et al. |
| 5,091,351 A | 2/1992 | Murakawa et al. |
| 5,108,581 A | 4/1992 | Aldridge |
| 5,527,436 A | 6/1996 | Cooker et al. |
| 5,601,937 A | 2/1997 | Isenberg |
| 5,624,493 A | 4/1997 | Wagh et al. |
| 5,904,837 A | 5/1999 | Fujiyama |
| 5,906,728 A | 5/1999 | Iaccino et al. |
| 5,951,850 A | 9/1999 | Ino et al. |
| 6,033,555 A | 3/2000 | Chen et al. |
| 6,084,142 A | 7/2000 | Yao et al. |
| 6,190,533 B1 | 2/2001 | Bradow et al. |
| 6,210,562 B1 | 4/2001 | Xie et al. |
| 6,280,593 B1 | 8/2001 | Wiese et al. |
| 6,293,979 B1 | 9/2001 | Choudhary et al. |
| 6,312,658 B1 | 11/2001 | Hufton et al. |
| 6,319,864 B1 | 11/2001 | Hannigan et al. |
| 6,336,791 B1 | 1/2002 | O'Toole |
| 6,531,515 B2 | 3/2003 | Moore, Jr. et al. |
| 6,656,346 B2 | 12/2003 | Ino et al. |
| 6,743,961 B2 | 6/2004 | Powers |
| 6,849,356 B2 | 2/2005 | Dow et al. |
| 6,852,901 B2 | 2/2005 | Hasenberg et al. |
| 6,979,757 B2 | 12/2005 | Powers |
| 7,019,187 B2 | 3/2006 | Powers |
| 7,045,554 B2 | 5/2006 | Raje et al. |
| 7,132,042 B2 | 11/2006 | Genetti et al. |
| 7,302,795 B2 | 12/2007 | Vetrovec |
| 7,374,664 B2 | 5/2008 | Powers |
| 7,378,561 B2 | 5/2008 | Olah et al. |
| 7,396,449 B2 | 7/2008 | Powers |
| 7,404,889 B1 | 7/2008 | Powers |
| 7,419,584 B2 | 9/2008 | Stell et al. |
| 7,460,333 B2 | 12/2008 | Akamatsu et al. |
| 7,550,642 B2 | 6/2009 | Powers |
| 7,592,290 B2 | 9/2009 | Hussain et al. |
| 7,642,292 B2 | 1/2010 | Severinsky |
| 7,744,747 B2 | 6/2010 | Halsey |
| 7,858,834 B2 | 12/2010 | Powers |
| 7,906,559 B2 | 3/2011 | Olah et al. |
| 7,972,498 B2 | 7/2011 | Buchanan et al. |
| 7,973,087 B2 | 7/2011 | Kibby et al. |
| 8,152,973 B2 | 4/2012 | Yamamoto et al. |
| 8,198,338 B2 | 6/2012 | Shulenberger et al. |
| 8,287,716 B2 | 10/2012 | Al-Sadah |
| 8,303,917 B2 | 11/2012 | Miyashiro et al. |
| 8,304,567 B2 | 11/2012 | Kadota et al. |
| 8,628,668 B2 | 1/2014 | Simonson |
| 8,816,137 B2 | 8/2014 | Olah et al. |
| 8,845,940 B2 | 9/2014 | Niven et al. |
| 8,951,333 B2 | 2/2015 | Cabourdin et al. |
| 9,085,497 B2 | 7/2015 | Jennings |
| 9,090,543 B2 | 7/2015 | Schoedel et al. |
| 9,096,806 B2 | 8/2015 | Abba et al. |
| 9,175,409 B2 | 11/2015 | Sivasankar et al. |
| 9,221,027 B2 | 12/2015 | Kuppler et al. |
| 9,242,230 B2 | 1/2016 | Moon et al. |
| 9,255,230 B2 | 2/2016 | Shafi et al. |
| 9,260,366 B2 | 2/2016 | Verhaak et al. |
| 9,279,088 B2 | 3/2016 | Shafi et al. |
| 9,284,497 B2 | 3/2016 | Bourane et al. |
| 9,284,502 B2 | 3/2016 | Bourane et al. |
| 9,296,961 B2 | 3/2016 | Shafi et al. |
| 9,303,323 B2 | 4/2016 | DiMascio et al. |
| 9,312,454 B2 | 4/2016 | Itoh et al. |
| 9,328,035 B1 | 5/2016 | Kuhn et al. |
| 9,435,404 B2 | 9/2016 | Goleski et al. |
| 9,555,367 B2 | 1/2017 | Masel et al. |
| 9,559,375 B2 | 1/2017 | Savinell et al. |
| 9,618,264 B1 | 4/2017 | Berdut-Teruel |
| 9,634,343 B2 | 4/2017 | Munier et al. |
| 9,675,979 B2 | 6/2017 | Hassell |
| 9,752,080 B2 | 9/2017 | Christensen et al. |
| 9,884,313 B2 | 2/2018 | Shen et al. |
| 9,963,392 B2 | 5/2018 | Deo et al. |
| 9,970,804 B2 | 5/2018 | Khousa et al. |
| 9,973,141 B2 | 5/2018 | Hammad et al. |
| 10,179,733 B2 | 1/2019 | Becker et al. |
| 10,252,243 B2 | 4/2019 | Fadhel et al. |
| 10,252,909 B2 | 4/2019 | Lofberg et al. |
| 10,329,676 B2 | 6/2019 | Kaczur et al. |
| 10,357,759 B2 | 7/2019 | D'Souza et al. |
| 10,422,754 B2 | 9/2019 | Al Hosani et al. |
| 2003/0233018 A1 | 12/2003 | Brown et al. |
| 2005/0211603 A1 | 9/2005 | Guillaume et al. |
| 2006/0171065 A1 | 8/2006 | Akamatsu et al. |
| 2008/0011644 A1 | 1/2008 | Dean |
| 2008/0011645 A1 | 1/2008 | Dean |
| 2008/0083648 A1 | 4/2008 | Bishop et al. |
| 2008/0194900 A1 | 8/2008 | Bhirud |
| 2008/0277314 A1 | 11/2008 | Halsey |
| 2008/0283445 A1 | 11/2008 | Powers |
| 2009/0050523 A1 | 2/2009 | Halsey |
| 2010/0089795 A1 | 4/2010 | Fujiyama et al. |
| 2010/0137458 A1 | 6/2010 | Erling |
| 2011/0021858 A1 | 1/2011 | Ramachandran et al. |
| 2011/0083996 A1 | 4/2011 | Shafi et al. |
| 2011/0132770 A1 | 6/2011 | Sala et al. |
| 2011/0247500 A1 | 10/2011 | Akhras et al. |
| 2013/0129610 A1 | 5/2013 | Kale |
| 2013/0220884 A1 | 8/2013 | Bourane et al. |
| 2013/0233766 A1 | 9/2013 | Shafi et al. |
| 2013/0248419 A1 | 9/2013 | Abba |
| 2015/0225295 A1 | 8/2015 | Mcandlish et al. |
| 2015/0337445 A1 | 11/2015 | Hasegawa et al. |
| 2015/0343416 A1 | 12/2015 | Fadhel et al. |
| 2016/0002035 A1 | 1/2016 | Ralston et al. |
| 2016/0264886 A1 | 9/2016 | Davydov |

(56) References Cited

U.S. PATENT DOCUMENTS

| | | |
|---|---|---|
| 2016/0333487 A1 | 11/2016 | Rodriguez |
| 2017/0050845 A1 | 2/2017 | Lofberg et al. |
| 2017/0292197 A1 | 10/2017 | Lei et al. |
| 2018/0057423 A1 | 3/2018 | Kimura et al. |
| 2019/0194074 A1 | 6/2019 | Amr et al. |
| 2021/0387929 A1 | 12/2021 | Fadhel et al. |

FOREIGN PATENT DOCUMENTS

| | | |
|---|---|---|
| CN | 111450841 | 7/2020 |
| DE | 102006020843 | 11/2007 |
| WO | 2000009633 | 2/2000 |
| WO | 2009073436 | 6/2009 |
| WO | 2010009077 | 1/2010 |
| WO | 2010009082 | 1/2010 |
| WO | 2010009089 | 1/2010 |
| WO | 2010143783 | 12/2010 |
| WO | 2015128045 | 9/2013 |
| WO | 2014160168 | 10/2014 |
| WO | 2015183200 | 12/2015 |
| WO | 2016207892 | 12/2016 |
| WO | 2019112555 | 6/2019 |

OTHER PUBLICATIONS

PCT International Search Report and Written Opinion in International Appln. No. PCT/US2022/011194, dated Apr. 22, 2022, 12 pages.

PCT International Search Report and Written Opinion in International Appln. No. PCT/US2021/036161, dated Sep. 9, 2021, 13 pages.

Sushil et al., "Catalytic applications of red mud, an aluminium industry waste: A review," Applied Catalysis B. Environmental, May 2008, 81(1-2): 64-77, 14 pages.

U.S. Appl. No. 16/899,254, filed Jun. 11, 2020, Fadhel et al.

Albrecht et al., "Unexpectedly efficient CO2 hydrogenation to higher hydrocarbons over non-doped Fe2O3," Applied Catalysis B: Environmental 204: 119-126, May 2017, 8 pages.

Bhuiyan, "Metathesis of Butene to Produce Propylene over Mesoporous Tungsten Oxide Catalyst: Synthesis, Characterization and Kinetic Modeling," A Thesis Presented to the Deanship of Graduate Studies, King Fahd University of Petroleum and Minerals, in Partial Fulfillment of the Requirements for the Degree of Master of Science in Chemical Engineering, Jun. 2013, 188 pages.

Chew et al., "Effect of nitrogen doping on the reducibility, activity and selectivity of carbon nanotube-supported iron catalysts applied in CO2 hydrogenation," Applied Catalysis A: General 482: 163-170, Jul. 2014, 29 pages.

Choi et al., "Carbon dioxide Fischer-Tropsch synthesis: A new path to carbon-neutral fuels," Applied Catalysis B: Environmental 202: 605-610, Mar. 2017, 6 pages.

Choi et al., "Hydrogenation of carbon dioxide over alumina supported Fe—K catalysts," Catalysis Letters 40: 115-118, Mar. 1996, 4 pages.

Cowie et al., "Naturally occurring radioactive material and naturally occurring mercury assessment of black powder in sales gas pipelines," Radiation Protection and Environment 42: 34-9, Jan.-Mar. & Apr.-Jun. 2019, 6 pages.

Cramer et al., "The Mechanism of Isomerization of Olefins with transition metal catalysts," Journal of the American Chemical Society, 88(15): 3534-3544, Aug. 5, 1966, 11 pages.

Dinesh et al., "Iron-based flow batteries to store renewable energies," Environmental Chemistry Letters, Feb. 2018, 12 pages.

Ding et al., "CO2 Hydrogenation to Hydrocarbons over Iron-Based Catalyst: Effects of Physico-Chemical Properties of Al2O3 Supports," I&EC Research, Industrial & Engineering Chemistry Research 53(45): 17563-17569, Oct. 2014, 30 pages.

Du et al., "Sodium Hydroxide Production from Seawater Desalination Brine: Process Design and Energy Efficiency," Environmental Science & Technology 52: 5949-5958, 2018, 10 pages.

Fang et al., "A Nanomesoporous Catalyst from Modifier Red Mud and Its Application for Methane Decomposition to Hydrogran Production," Article ID 6947636, Hindawi Publishing Corporation, Journal of Nanomaterials, 2016, 8 pages.

Godoy et al., "210Pb content in natural gas pipeline residues ("black-powder") and its correlation with the chemical composition," Journal of Environmental Radioactivity 83: 101-111, 2005, 12 pages.

Grafe et al., "Bauxite residue issues: IV. Old obstacles and new pathways for in situ residue bioremediation," Hydrometallurgy 108: 46-59, 2011, 14 pages.

Hu et al., "Hydrothermally stable MOFs for CO2 hydrogenation over iron-based catalyst to light olefins," Journal of CO2 Utilization, 15: 89-95, 2016, 7 pages.

Hua et al., "Transformation of 2-Butene into Propene on WO3/MCM-48: Metathesis and Isomerization of n-Butene," Catalysts 8: 585, 2018, 11 pages.

Kurtoglu and Uzun, "Red Mud as an Efficient, Stable, and Cost-Free Catalyst for Cox-Free Hydrogren Production from Ammonia," Scientific Reports, 6:32279, 2016, 8 pages.

Lee et al., "Selective Positional Isomerization of 2-Butene over Alumina and La-promoted Alumina Catalysts," J. Ind. Eng. Chem. 13(7): 1062-1066, Dec. 2007, 5 pages.

Life-greenlysis.eu [online], "Hydrogen and Oxygen production via electrolysis powered by renewable energies to reduce environmental footprint of a WWTP.," Greenlysis, URL <www.life-greenlysis.eu>, 2010-2012, 16 pages.

Liu et al. "Fe—MOF-derived highly active catalysts for carbon dioxide hydrogenation to valuable hydrocarbons," Journal of CO2 Utilization 21:100-107, Oct. 2017, 8 pages.

Liu et al., "Preparation of Modified Red Mud-Supported Fe Catalysts for Hydrogran Production by Catalytic Methane Decomposition," Article ID 8623463, Hindawi, Journal of Nanomaterials, 2017, 11 pages.

Liu et al., "Pyrolyzing ZIF-8 to N-doped porous carbon facilitated by iron and potassium for CO2 hydrogenation to value-added hydrocarbons," Journal of CO2 Utilization 25: 120-127, May 2018, 8 pages.

Madadkhani, "Red mud as an Ironbased Catalyst for Catalytic Cracking of Naphthalene," a Thesis Submitted in Partial Fulfillment of the Requirement for the Degree of Master of Applied Science in the Faculty of Graduate and Postdoctoral Studies (Chemical and Biological Engineering), The University of British Columbia, Dec. 2016, 192 pages.

Morrison, "Cis-trans Isomerization of Olefins by Intramolecular Energy Transfer," Journal of the American Chemical Society 87(4): 932, Feb. 1965, 1 page.

Naik et al. "Carbon Dioxide sequestration in cementitious products," Report No. CNU-2009-02, REP-640, Department of Civil Engineering and Mechanics, College of Engineering and Applied Science, University of Wisconsin-Milwaukee, Jan. 2009, 53 pages.

Nam et al., "Catalytic conversion of carbon dioxide into hydrocarbons over iron supported on alkali ion-exchanged Y-zeolite catalysts," Applied Catalysis A: General 179: 155-163, Apr. 1999, 9 pages.

Nam et al., "Catalytic Conversion of Carbon dioxide into hyrdrocarbons over zinc promoted iron catalysts," Energy onvers. Manage. 38: S397-S402, 1997, 6 pages.

Ndlela et al., "Reducibility of Potassium-Promoted Iron Oxide under Hydrogen Conditions," Ind. Eng. Chem. Res. 42: 2112-2121, 2003, 10 pages.

Numpilai et al., "Pore size effects on physicochemical properties of Fe—Co/K—Al2O3 catalysts and their catalytic activity in CO2 hydrogenation to light olefins," Applied Surface Science 483: 581-592, Jul. 2019, 12 pages.

Pall.com [online], "Cyclo-Filter System," retrieved from URL <https://www.pall.com/en/oil-gas/midstream/midstream-black-powder.html>, retrieved on Jun. 16, 2020, available on or before 2020, 4 pages.

Pavlov et al., "Processes of Synthesis of 1-Butene from 2-Butene by the Positional Isomerization on Sulfocation Exchangers," Russian Journal of Applied Chemistry, 82:6, 2009, 1117-1122, 6 pages.

(56) References Cited

OTHER PUBLICATIONS

Ramirez et al., "Metal Organic Framework—Derived Iron Catalysts for the Direct Hydrogenation of CO2 to Short Chain Olefins," ACS Catalysis 8:9174-9182, 2018, 32 pages.

Researchandmarkets.com [online], "Global 1 Butene Demand—Supply and Price Analysis," 2002-2021, retrieved on Jan. 26, 2021, retrieved from URL <https://www.researchandmarkets.com/reports/3752113/global-1-butene-demand-supply-and-price-analysis>, 1 page.

Russkikh et al. "Turning Waste into Value: Potassium-Promoted Red Mud as an Effective Catalyst for the Hydrogenation of CO2," ChemSusChem 13.11, 2020, 2981-2987, 7 pages.

Russkikh et al., "Red mud as an efficient catalyst in turning CO2 hydrogenation," Chemical Science Seminar, retrieved from URL: <https://pse.kaust.edu.sa/events/red-mud-as-an-efficient-catalyst-in-turning-co2-hydrogenationinto-useful-products>, Oct. 13, 2019, KAUST, 2019, 1 page, (abstract only).

Shop.pall.com (online), "Black Powder Filter," retrieved from URL <https://shop.pall.com/us/en/search?SearchTerm=black+powder+filter&resetsearch=true>, retrieved on Jun. 16, 2020, available on or before 2020, 7 pages.

Thach et al., "Further Improvements in Isomerization of Olefins in Solvent-free conditions," retrieved from URL: <https://www.tandfonline.com/doi/abs/10.1080/00397919308011226>, Journal of Synthetic Communications 23:10, Nov. 1992, 1379-1384, 3 pages, (abstract only).

Van Beurden, "On the Catalytic Aspects of Stream-Methane Reforming: A Literature Survey," ECN-I--04-003, retrieved from URL: <https://publicaties.ecn.nl/PdfFetch.aspx?nr=ECN-I--04-003>, Dec. 2004, 27 pages.

Visconti et al., "CO2 Hydrogentation to Lower Olefins on a High Surface Area K—Promoted Bulk FE-Catalyst," Applied Catalyysis B: Environmental 200:530-542, 2017, 44 pages.

Wahyudi et al., "Utilization of Modified Red Mud as a Heterogeneous Base Catalyst for Transesterification of Canola Oil," Journal of Chemical Engineering of Japan, 50:7, 2017, 561-567, 7 pages.

Wang et al., "Fe—Cu Bimetallic Catalysts for Selective CO2 Hydrogenation to Olefin-rich C2+ Hydrocarbons," I&EC Research, Industrial & Engineering Chemistry Research 57(13): 4535-4542, Feb. 2018, 37 pages.

Wei et al., "New insights into the effect of sodium on Fe3O4-based nanocatalysts for CO2 hydrogenation to light olefins," Catalysis Science & Technology 6(13): 4786-4793, 2016, 8 pages.

Yensen et al., "Open source all-iron battery for renewable energy storage," HardwareX 6: e00072, 2019, 11 pages.

You et al., "Hydrogenation of carbon dioxide to light olefins over non-supported iron catalyst," Chinese Journal of Catalysis 34(5): 956-963, May 2013, 8 pages.

\* cited by examiner

400

500

ACID MODIFIED RED MUD AS A CATALYST FOR OLEFIN ISOMERIZATION

BACKGROUND

The polymerization of olefins often uses comonomers to affect the final properties, such as density, crystallinity, and the like. The comonomers are generally alpha-olefins, such as 1-butene, 1-hexene, and 1-octene, among others. Alpha-olefins are also important feedstocks for numerous other products, including additives for drilling fluids, lubricants, synthetic oils, plasticizers, and other products.

One of the most important alpha-olefins is 1-butene. The market size projection for 1-butene has been projected to pass four billion USD in 2021. Satisfying the projected demand for 1-butene through the currently used method of ethylene dimerization may be impractical due to costs and its competitive use in polyethylene.

SUMMARY

An embodiment described in examples herein provides a method for using an acid modified red mud (AMRM) catalyst for olefin isomerization. The method includes forming the AMRM catalyst by dissolving red mud in water to form a red mud solution, neutralizing the red mud solution with an acid, and forming a precipitate by adding a base to the red mud solution. The precipitant is filtered from the red mud solution, dried, and ground to form particles of less than 100 µm. The particles are calcined to form the AMRM catalyst. A butene feedstock is flowed over the AMRM catalyst in an isomerization reactor. 1-Butene is separated from a reactor effluent.

Another embodiment described in examples herein provides a method of making an acid modified red mud (AMRM) catalyst for olefin isomerization. The method includes dissolving red mud in water to form a red mud solution and neutralizing the red mud solution with an acid. A precipitant is formed by adding a base to the red mud solution and the precipitant is filtered from the red mud solution. The precipitant is dried, calcined, and ground to form the AMRM catalyst with a particle size of less than about 100 µm.

Another embodiment described in examples herein provides an isomerization unit for producing a 1-butene product stream from a butene feedstock. The isomerization unit includes an upstream purification system to separate a feed stream that includes trans-2-butene and cis-2-butene from an initial feedstock, generating the butene feedstock. The isomerization unit further includes a reactor including an acid modified red mud (AMRM) catalyst to isomerize the trans-2-butene and cis-2-butene to form 1-butene, and a product purification system to isolate the 1-butene product stream from an effluent from the reactor.

DETAILED DESCRIPTION

Alpha olefins used as comonomers for polymerization, such as 1-butene, 1-hexene, and 1-octene, may be produced by the isomerization of secondary olefins, for example, isolated from refinery feed streams. For example, one method for the production of 1-butene is the isomerization of 2-butene, which is an available material in refinery feed streams. The isomerization proceeds with aid of catalysts, such as $SiO_2$, $TiCl_3$, organo-aluminum, or zinc chromium ferrite ($Zn_xCr_yFe_zO_4$), acidized clay, alumina, or MgO catalysts, among others. However, improvements in cost, durability, selectivity, and efficiency of catalysts are desirable.

Red mud is a waste product generated during alumina production in the Bayer process, which is responsible for more than 95% of all alumina produced in the world. In this process, each ton of aluminum oxide that is produced results in 0.3 to 2.5 tons of bauxite tailings, or red mud. Consequently, about 155 million tons of red mud are created annually with worldwide storage at over 3.5 billion tons in 2014. Accordingly, red mud is a low cost material that is in high supply. Although red mud has significant heterogeneity, the generic composition is shown in Table 1. The complex mixture of metals indicates that red mud and modified red muds may be effective catalysts for the isomerization of olefins, such as 2-butene to 1-butene.

TABLE 1

| The generic composition of global red mud | | | | | |
|---|---|---|---|---|---|
| Component | $Fe_2O_3$ | $Al_2O_3$ | $SiO_2$ | $Na_2O$ | CaO | $TiO_2$ |
| Percentage | 30-60% | 10-20% | 3-50% | 2-10% | 2-8% | 10% |

Methods for the use of acid modified red mud (AMRM) as a catalyst for olefin isomerization are described herein. The acid modification of the red mud increases the surface area of the red mud substantially. In one example, the surface area increased from about 16 $m^2/g$ to about 142 $m^2/g$. For this reason, the AMRM catalyst shows a substantial increase in performance of over unmodified red mud used as a catalyst. Further, the metals content of the AMRM catalyst provides improved performance over other isomerization catalysts, such as $SiO_2$ and MgO.

Figure 1:
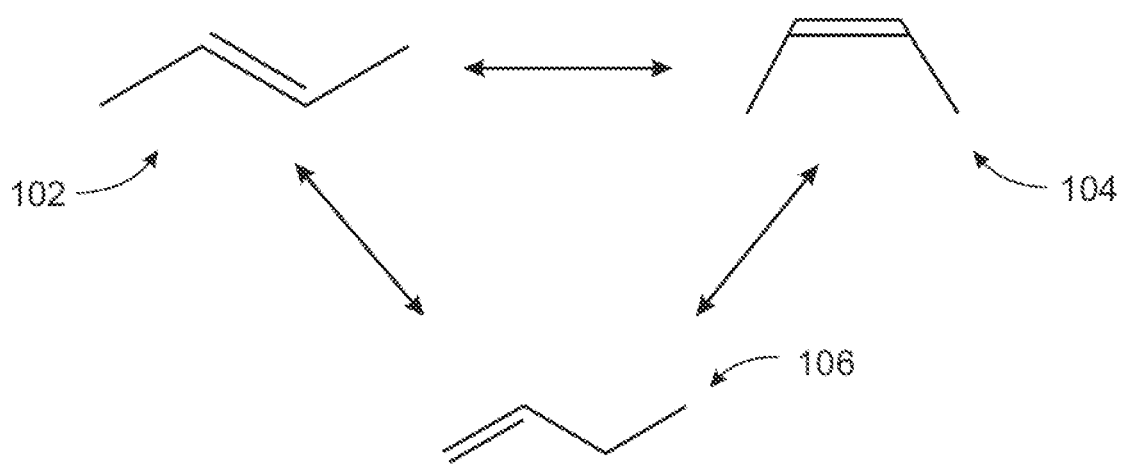
FIG. 1 is a reaction scheme showing the inter-conversions of 2-butene and 1-butene by isomerization.

FIG. 1 is a reaction scheme 100 showing the inter-conversions of 2-butene and 1-butene by isomerization. In the reaction scheme 100, trans-2-butene 102, cis-2-butene 104, and 1-butene 106 can be isomerized to each other. The lowest energy configuration is the trans-2-butene 102, and thus, a catalyst is used to form the 1-butene 106.

In embodiments described in examples herein, an AMRM catalyst is used to isomerize the 2-butene isomers 102 and 104 to produce 1-butene. This takes advantage of the mixture of metals constituting red mud, which include Ti, Fe, and Al. The mixture of the metal compounds in the red mud may enhance the isomerization yield and selectivity, for example, as compared to MgO or $SiO_2$ catalysts. Further, red mud is a waste material of negligible cost, which improves the competitive advantage over synthesized catalysts containing MgO or $SiO_2$.

Accordingly, even at comparable rates of isomerization yield and selectivity, and including the cost of the acid modification, the low cost of the red mud makes the use of the AMRM catalyst favorable over higher cost catalysts. Further, the acid modification improves the performance of the AMRM catalyst over an unmodified red mud catalyst.

Figure 2:
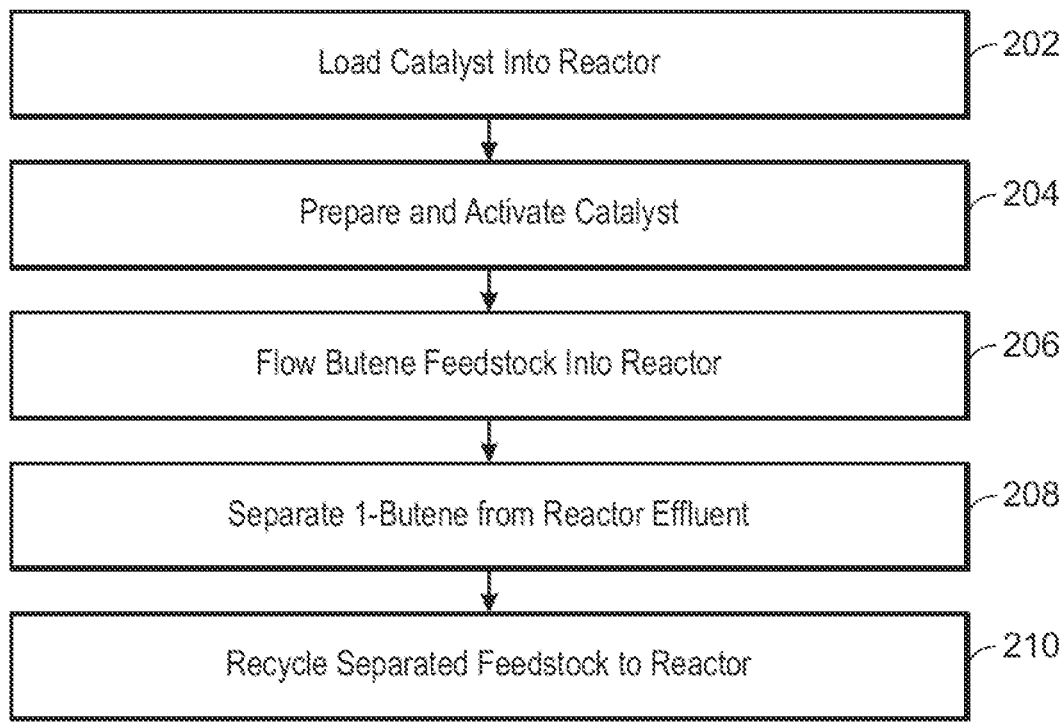
FIG. 2 is a method for using an acid modified red mud (AMRM) catalyst to convert 2-butene in a feedstock to 1-butene.

FIG. 2 is a method 200 for using an AMRM catalyst to convert 2-butene in a feedstock to 1-butene. Although the isomerization described in examples herein is 2-butene to 1-butene, it can be noted that the AMRM catalyst may be used for isomerization of other materials, for example, to form 1-octene, 1-hexene, and the like. The method 200 begins at block 202, with loading the AMRM catalyst into the reactor.

Figure 3:
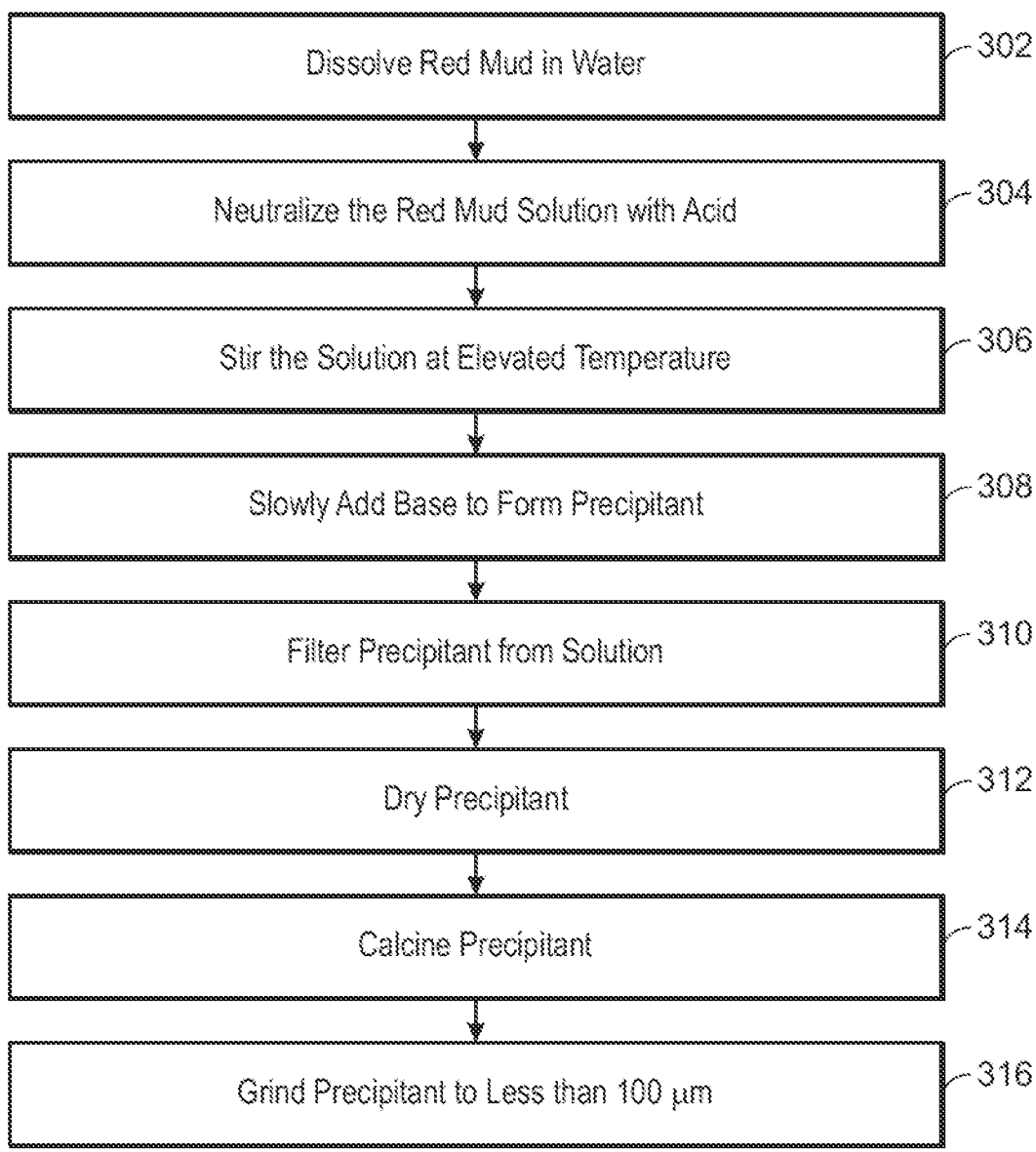
FIG. 3 is a method for preparing an AMRM catalyst for olefin isomerization.

At block 204, the AMRM catalyst, for example, prepared by the procedure of FIG. 3, is activated. As described in the examples, the prepared AMRM catalyst is calcined to drive off excess moisture and volatile components. The drying is performed under air at a temperature of between about between about 85° C. and about 125° C., or at a temperature of between 95° C. and about 115° C., or at about 105° C. The drying may be performed for between about 40 minutes and about 6 hours, or for between about 2 hours and about 5 hours, or for about 4 hours. The catalyst is further calcined for activation, for example, by the generation of surface groups. The activation may be performed under a flow of an inert gas. The activation is performed at a temperature of between about 500° C. and about 700° C., or at a temperature of between 550° C. and about 650° C., or at about 600° C. The activation may be performed for between about 2 hours and about 6 hours, or for between about 3 hours and about 5 hours, or for about 4 hours.

At block 206, the 2-butene feedstock is flowed into the reactor for isomerization into the 1-butene. In some embodiments described herein, the 2-butene feedstock is a mixture of cis-2-butene and trans-2-butene, for example, at a 50-50 ratio. In various embodiments, such as in commercial usage, the 2-butene feedstock is a refinery stream that includes a number of hydrocarbons with boiling points in a range. For example, the 2-butene feedstock may be a light fraction from a hydrocracking unit, having a boiling point range of about −30° C. to about 40° C., about −20° C. to about 10° C., or about −10° C. to about 0° C. A narrower range of boiling points may be indicative of a feedstock that is higher in cis-2-butene and trans-2-butene, providing a higher purity 1-butene product stream, and decreasing the purification required before sales. The butene feedstock is flowed through the reactor at a weight-hour space velocity (WHSV) ($hr^{-1}$) of between about 400 $hr^{-1}$ and about 1400 $hr^{-1}$, or between about 650 $hr^{-1}$ and about 1150 $hr^{-1}$, or about 900 $hr^{-1}$.

At block 208, the 1-butene product is separated from the reactor effluent. The 1-butene may then be provided to other processes, such as polymerization of polyolefins. At block 210, the separated effluent, for example, including unreacted 2-butene, may be recycled to the reactor to increase yields. The separated effluent may be sent to purification systems upstream of the reactor to remove other hydrocarbons or may be provided directly to the reactor, for example, by being mixed with the initial feedstock.

FIG. 3 is a method 300 for preparing an AMRM catalyst for olefin isomerization. The method 300 begins at block 302 with the dissolution of the red mud in water. The water may be purified, for example, distilled or deionized, or may be tap water. Generally, any water source having low total dissolved solids may be used, as the variation of the composition of the final AMRM catalyst will not be substantially increased over the natural variation of a red mud. However, it can be noted that water that is higher in potassium, sodium, or sulfates, among other ions, may affect the catalyst activity. The dissolution may be aided by stirring, sonication, and the like. The amount of the red mud used may be between about 5% and about 20% of the total weight of the solution, or between about 7.5% and about 15% of the total weight of the solution, or about 10% of the total weight of the solution.

At block 304, the red mud solution is neutralized with acid. For example, as formed, the red mud solution may have a pH of greater than about 10 or greater than about 8. The acid is added to bring the pH to about 7, or about 6, or about 5, or less. Lowering the pH enhances the solubility and homogeneity of the red mud solution. In some embodiments, the acid solution is diluted hydrochloric acid, for example, a 2 wt. % hydrochloric acid solution, a 4 wt. % hydrochloric acid solution, or a 10 wt. % hydrochloric acid solution.

At block 306, the neutralized red mud solution is stirred at an elevated temperature over a period of time to complete the dissolution. For example, the red mud solution may be heated to a temperature of between about 40° C. and about 100° C., or a temperature of between about 50° C. and about 70° C., or to a temperature of about 60° C. The red mud solution may be stirred at the elevated temperature for greater than about 1 hour, greater than about 2 hours, or for about 3 hours or greater.

At block 308, a base is slowly added to the red mud solution to form a precipitant. In some embodiments, the base is ammonium hydroxide. In some embodiments, the base is sodium hydroxide or potassium hydroxide, among others. As noted herein, though, the presence of other ions, such as sodium or potassium ions, may affect the catalyst activity. The base is added while stirring until the pH reaches about 8. At block 310, the precipitant is filtered from the red mud solution. For example, the filtration may be performed using a vacuum filtration apparatus at lab or commercial scales.

At block 312, the precipitant is dried. This may be performed, for example, at a temperature of greater than 60° C., or greater than 80° C., or greater than 100° C. The drying may be conducted under a vacuum or may be performed under ambient atmospheric conditions. The drying is performed for greater than 4 hours, greater than 8 hours, or greater than 12 hours, for example, depending on the temperature and atmospheric conditions.

At block 314, the precipitant is calcined. In various embodiments, the calcination is performed at a temperature of greater than about 400° C., or at a temperature of greater than about 500° C., or at a temperature equal to or greater than about 600° C. In various embodiments, the calcination is performed for a period of time greater than about 1 hour, greater than about 2 hours, greater than about 4 hours, or greater than about 8 hours.

At block 316, the calcined precipitant is ground to form fine particles of the final AMRM catalyst. In various embodiments, the particle size is less than about 100 μm, less than about 90 μm, less than about 80 μm, less than about 70 μm, less than about 60 μm, or smaller. The particle size may be chosen to fit the reactor and reaction conditions, for example, a fixed bed reactor may use a larger particle size while a flowing bed reactor or a fluidized bed reactor may use a smaller particle size.

In commercial usage, the catalyst may be dried and activated at a remote production facility, before being brought to the isomerization unit and loaded into the reactor. Any number of combinations of this may be performed. For example, the catalyst may be dried at the remote production facility and activated after being loaded into the commercial isomerization reactor.

Figure 4:
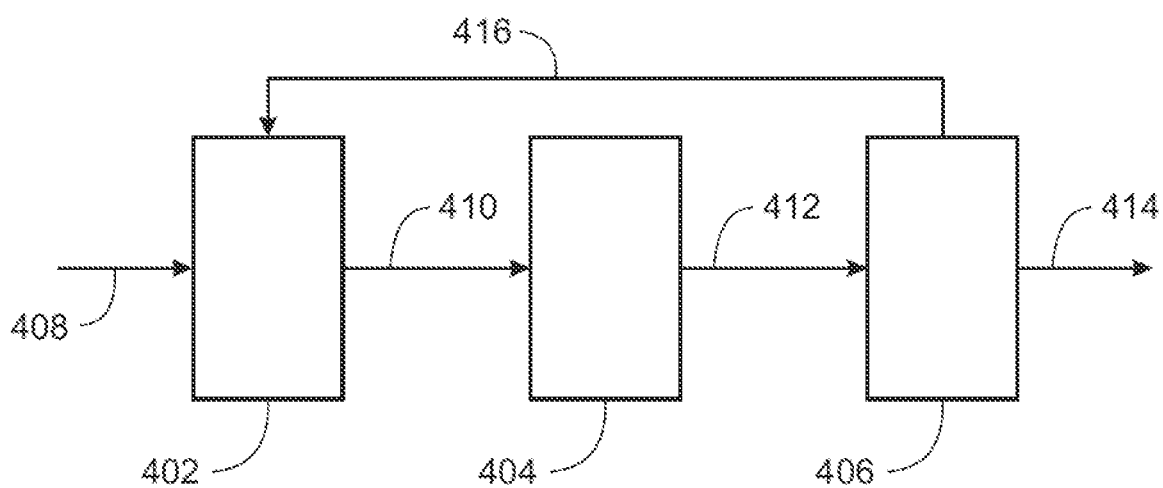
FIG. 4 is an isomerization unit for implementing olefin isomerization using an AMRM catalyst.

FIG. 4 is an isomerization unit 400 for implementing olefin isomerization using an AMRM catalyst. The isomerization unit 400 may be part of a refinery system, producing a number of different hydrocarbon streams. In this example, the isomerization unit 400 includes three units, an upstream purification system 402, a reactor 404, and a product purification system 406.

The initial feedstock 408 is fed to the upstream purification system 402. In various embodiments, the upstream purification system 402 includes a distillation column, a cryogenic distillation column, a flash vessel, and the like. Other streams (not shown), having different boiling point ranges, are separated out in the upstream purification system 402 and sent to another processing units. An isomerization feedstock stream 410, for example, having a boiling point range that includes trans-2-butene and cis-2-butene, is provided to the reactor 404.

In the reactor 404, the isomerization feedstock stream 410 is flowed over the red mud, which catalyzes the isomerization reaction of at least a portion of the 2-butene feedstocks to a 1-butene product. A reactor effluent stream 412 is then provided to the product purification system 406. In some embodiments, the reactor 404 is a standard isomerization reactor used in a refinery.

In the product purification system 406, the 1-butene product is separated and provided as a product stream 414. In various embodiments, the product purification system 406 includes a distillation column, a cryogenic distillation column, a flash vessel, and the like. The product stream 414 may be sold to polyolefin manufacturers, used in other processes to form other products, and the like. Other streams (not shown) from the product purification system 406 may be sent to other processing units. In some implementations, a recycle stream 416 is returned from the product purification system 406 to the upstream purification system 402 after removal of the 1-butene product. This may be performed to allow the recovery of unreacted trans-2-butene and cis-2-butene to increase the overall yield of the process. In other implementations, the recycle stream 416 is combined with the isomerization feedstock stream 410 directly, and fed to the reactor 404.

EXAMPLES

Formation of the AMRM Catalyst

Acid modified red mud catalyst was prepared using a homogeneous precipitation process. First, a red mud solution was formed by dissolving 10 g of dry red mud in 100 ml deionized water. The red mud solution was ultrasonicated for 3 min, and then it was neutralized by adding 40.5 ml of 37% hydrochloric acid mixed with 359.5 ml of deionized water.

The resulting solution was heated at 60° C. in a water bath and magnetically stirred for 3 hours. After that, a precipitant was formed from the solution by slowly adding aqueous ammonia (around 30 ml of $NH_4OH$) while stirring until the pH reached 8. After that, the solution was filtered to isolate the precipitant, which was dried in an oven at 105° C. overnight and calcined at 600° C. for 4 hours. The final product was ground to have particle size less than 70 μm.

Characterization of AMRM Catalyst

The surface area of the AMRM catalyst, the total pore volume, and the pore size were measured using a Brunauer-Emmett-Teller (BET) technique. These measurements may be performed, for example, using the procedures in the ISO 9277 standard, "Determination of the specific surface area of solids by gas adsorption—BET method," Second Edition, 1 Sep. 2010. The BET results of the AMRM catalyst compared with unmodified RM are shown in Table 1.

TABLE 1

BET results of AMRM catalyst compared with unmodified RM

| Sample | Surface Area ($m^2/g$) | Total Pore Volume ($cm_3/g$) | Pore Size (Å) |
|---|---|---|---|
| RM | 16 | 0.0530 | 133.668 |
| AMRM | 142 | 0.3164 | 89.210 |

Elemental analyses were performed by X-ray Fluorescence (XRF) analysis. The XRF analysis was performed on a Horiba® XGT-7200. The X-ray tube is equipped with an Rh target, voltage was set at 30 kV, no X-ray filter was used, and analysis preset time was 400 s. Before measurement, samples were placed on a double-sized tape (NICETACK™, Prod. No NW-15) and then placed in the chamber, which was then degassed. The results are an average of four measurements were taken.

The composition of Saudi Arabian red mud is shown in Table 2 along with the composition of the acid modified red mud (AMRM). The red mud composition listed in Table 2 is the comprehensive composition, which includes both major and minor constituents. The mixture of metals is thought to grant red mud a performance advantage over other isomerization catalysts, especially MgO and $SiO_2$.

Comparative Catalyst Tests

The performance of an acid modified Saudi Arabian red mud sample in the isomerization of a mixture of trans-2-butene and cis-2-butene to 1-butene was evaluated at different temperatures, 450° C., 500° C., and 550° C. As red mud is a waste material, the composition is heterogeneous, with a 5%, or higher, variation in the composition. The variations in composition do not substantially affect the products or selectivity.

The results of the isomerization were compared to MgO and $SiO_2$ commercial catalysts, as well as to an unmodified Saudi Arabian red mud (RM) catalyst. The experimental runs were performed in a BTRS reactor unit from Autoclave Engineers division of Parker Hannifin Corp, having 9 mm ID and 30 cm length. The reactor is a stainless steel reactor with four different MFC units to control the flowing gases. The maximum temperature of the reactor system is 800° C. and the maximum pressure is 20 bar. The amount of catalyst used in each run was 2 mL (0.65 g).

TABLE 2

Typical composition of Saudi Arabian Red Mud in weight percent.

| Component | RM (from source) | AMRM |
|---|---|---|
| $Al_2O_3$ | 23.34 | 26 |
| CaO | 6.82 | 4.9 |
| $CeO_2$ | 0.09 | 0.174 |
| Cl | 0.03 | 0.204 |
| $Cr_2O_3$ | 0.15 | 0.15 |
| $Fe_2O_3$ | 29.45 | 34 |
| $Ga_2O_3$ | 0.01 | 0.015 |
| $HfO_2$ | 0.1 | 0.036 |
| $K_2O$ | 0.07 | 0.02 |
| MgO | 0.07 | 0.176 |
| MnO | 0.06 | 0.067 |

TABLE 2-continued

Typical composition of Saudi Arabian Red Mud in weight percent.

| Component | RM (from source) | AMRM |
|---|---|---|
| $Na_2O$ | 4.74 | 0.5 |
| $Nb_2O_5$ | 0.03 | 0.035 |
| $P_2O_5$ | 0.16 | 0.025 |
| PbO | 0.03 | 0.04 |
| $Sc_2O_3$ | 0.02 | 0.027 |
| $SiO_2$ | 23.1 | 15 |
| $SO_3$ | 0.09 | 0.33 |
| SrO | 0.36 | 0.22 |
| $ThO_2$ | 0.02 | 0.04 |
| $TiO_2$ | 10 | 16.5 |
| ZnO | 0.01 | 0.012 |
| $ZrO_2$ | 0.43 | 0.46 |
| $Y_2O_3$ | 0.02 | 0.021 |

Figure 5:
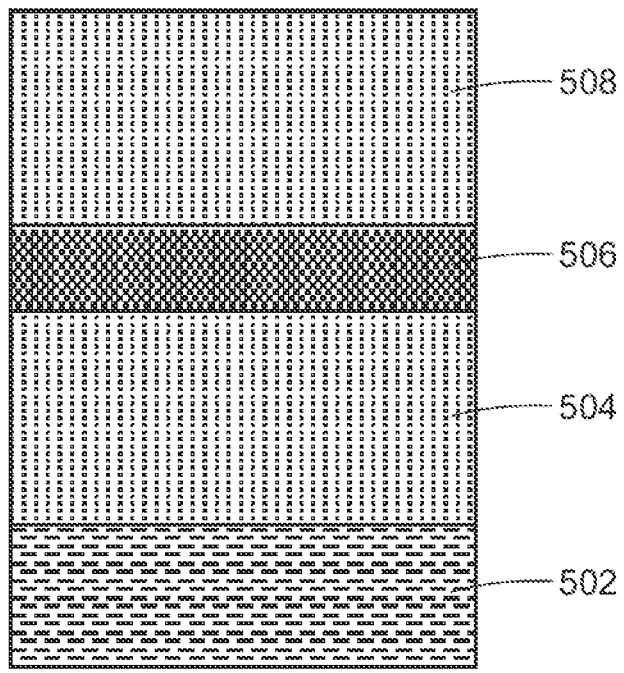
FIG. 5 is a schematic diagram of an experimental reactor tube for testing the conversion of 2-butene to 1-butene using a red mud catalyst.

FIG. 5 is a schematic diagram of an experimental reactor tube 500 for testing the conversion of 2-butene to 1-butene using a red mud catalyst. To hold the material in place a layer of quartz wool 502 is inserted into the experimental reactor tube 500. An initial layer 504 of 14 g of silicon carbide is poured over the quartz wool 502. A catalyst layer 506 including about 2 mL of catalyst is inserted into the experimental reactor tube 500. For the red mud catalyst, the 2 mL corresponds to about 0.65 g. Finally, a top layer 508 of about 17 g of silicon carbide is poured over the catalyst layer 506. The experimental reactor tube 500 is then inserted into the BTRS catalyst testing system.

Prior to evaluation, each catalyst sample was calcined under air at 650° C. to remove moisture or volatile gases, if present. The catalyst sample was then activated at 550° C. inside the reactor for 4 hrs under nitrogen. The 2-butene feed is a mixture of 50% cis-2-butene and 50% trans-2-butene. The concentration of 2-butene employed in the evaluation was 15% (5 ml) diluted with $N_2$ (25 ml).

The amounts of hydrocarbons in the reactor effluent streams were measured by gas chromatography. This was performed using an Agilent GC-7890B instrument from Agilent. The column was a capillary column (HP-Al/KCL (50 mm×0.53 mm×15 µm) with an $N_2$ stationary phase and He carrier gas. A hybrid detector including a flame ionization detector (FID) and a thermal conductivity detector (TCD) was used. The flow rate of the carrier gas was 15 ml/min. After injection, the temperature was ramped from 50° C. to 170° C. over a time span of 10 min., then the temperature was held at 220° C. for 15 min., before being cooled to the starting temperature.

From the GC results, yields and selectivities were calculated by the following formulas:

$$\text{Yield} = \text{Conversion of butenes} \times \text{Selectivity of the product (1-butene)}$$

$$\text{Conversion} = 100 - (\text{CisButene Yield} + \text{TransButene Yield})$$

$$\text{Conversion-}C4 = 100 - (\text{Cis-2-Butene Yield} + \text{Trans-2-Butene Yield})$$

$$\text{Selectivity} = \frac{\text{Yield of Product}}{\text{Conversion}} \times 100$$

In these formulas, yield represents the yield of 1-butene as obtained through the GC Retention Factor. The conversion of 2-butene (cis and trans 2-butene) is also obtained though GC retention factor.

Figure 6:
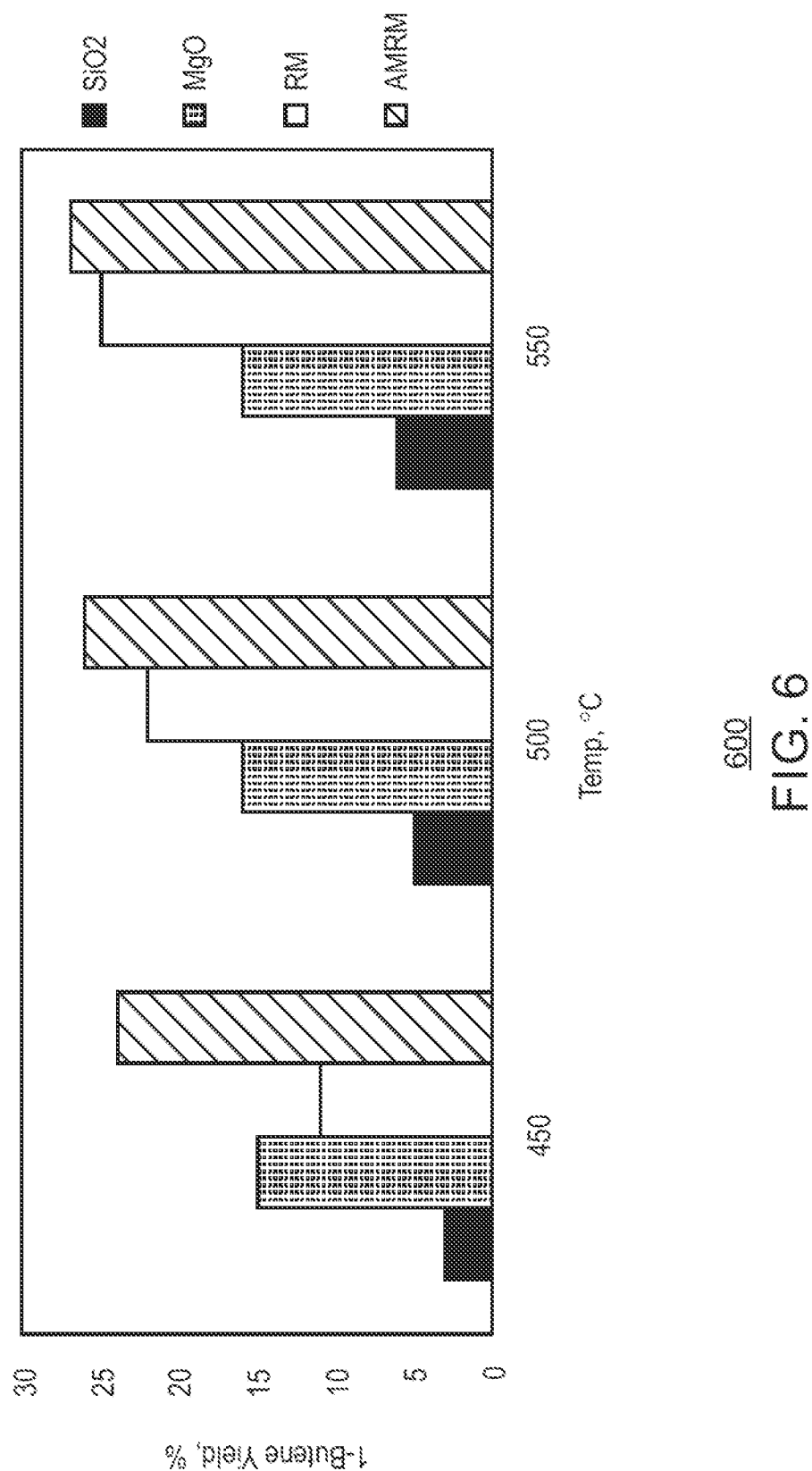
FIG. 6 is a bar chart showing the comparative yield of four catalysts in the conversion of 2-butene to 1-butene.

FIG. 6 is a bar chart 600 showing the comparative yield of four catalysts in the conversion of 2-butene to 1-butene. At all three tested temperatures, 450° C., 500° C., and 550° C., the AMRM catalyst provided a significantly higher yield of 1-butene than the other catalysts, including $SiO_2$, MgO, and unmodified red mud.

As described herein, red mud was modified with acid, substantially increasing its surface area from 16 $m^2/g$ to 142 $m^2/g$. The increased surface area, among other factors, increased the isomerization yield by 140% for 1-butene production from 2-butene, when compared to unmodified red mud. In addition, the proposed red mud modification enhanced the 2-butene isomerization yield by 66% and 733%, when compared to the commercially utilized catalysts of MgO and $SiO_2$, respectively. The yield increase took place at 450° C. as illustrated in FIG. 6, which will reduce the energy used in commercial implementations and, thus, lower $CO_2$ emissions.

An embodiment described in examples herein provides a method for using an acid modified red mud (AMRM) catalyst for olefin isomerization. The method includes forming the AMRM catalyst by dissolving red mud in water to form a red mud solution, neutralizing the red mud solution with an acid, and forming a precipitant by adding a base to the red mud solution. The precipitant is filtered from the red mud solution, dried, and ground to form particles of less than 100 µm. The particles are calcined to form the AMRM catalyst. A butene feedstock is flowed over the AMRM catalyst in an isomerization reactor. 1-Butene is separated from a reactor effluent.

In an aspect, the method further includes calcining the AMRM catalyst to activate the AMRM catalyst at a temperature of between about 400° C. and about 700° C. for between about 2 hours and about 6 hours. In an aspect, the method further includes calcining the AMRM catalyst to activate the AMRM catalyst at a temperature of between about 500° C. and about 600° C. for between about 3 hours and about 5 hours. In an aspect, the method further includes calcining the AMRM catalyst to activate the AMRM catalyst at a temperature of about 550° C. for about 4 hours.

In an aspect, the butene feedstock is obtained from an upstream purification system in a refinery. In an aspect, the butene feedstock is obtained with a boiling point range of between about −30° C. and about 40° C. In an aspect, the butene feedstock is obtained with a boiling point range of between about −20° C. and about 10° C. In an aspect, the butene feedstock is obtained with a boiling point range of between about −10° C. and about 0° C.

In an aspect, the butene feedstock is flowed over the AMRM catalyst at a weight-hour space velocity of between about 400 $hr^{-1}$ and 1300 $hr^{-1}$. In an aspect, the butene feedstock is flowed over the AMRM catalyst at a weight-hour space velocity of between about 650 $hr^{-1}$ and 1150 $hr^{-1}$. In an aspect, the butene feedstock is flowed over the AMRM catalyst at a weight-hour space velocity of about 900 $hr^{-1}$.

In an aspect, the 1-butene is separated from the reactor effluent in a distillation column. In an aspect, the reactor effluent is returned to an upstream purification system after removal of the 1-butene from the reactor effluent. In an aspect, the reactor effluent is combined with the butene feedstock after separating the 1-butene from the reactor effluent.

Another embodiment described in examples herein provides a method of making an acid modified red mud (AMRM) catalyst for olefin isomerization. The method includes dissolving red mud in water to form a red mud solution and neutralizing the red mud solution with an acid. A precipitant is formed by adding a base to the red mud solution and the precipitant is filtered from the red mud solution. The precipitant is dried, calcined, and ground to form the AMRM catalyst with a particle size of less than about 100 μm.

In an aspect, the red mud is dissolved in the water at a concentration of about 10 wt. %. In an aspect, the acid is added until the pH of the red mud solution is less than about 7. In an aspect, the base is added until the pH of the red mud solution is greater than about 8. In an aspect, the precipitant is dried at a temperature of greater than about 100° C. for a least about 8 hours.

In an aspect, the precipitant is calcined at a temperature of between about 500° C. and about 800° C. for between about 2 hours and about 6 hours. In an aspect, the precipitant is calcined at a temperature of between about 600° C. and about 700° C. for between about 3 hours and about 5 hours. In an aspect, the precipitant is calcined at a temperature of about 600° C. for about 4 hours.

Another embodiment described in examples herein provides an isomerization unit for producing a 1-butene product stream from a butene feedstock. The isomerization unit includes an upstream purification system to separate a feed stream that includes trans-2-butene and cis-2-butene from an initial feedstock, generating the butene feedstock. The isomerization unit further includes a reactor including an acid modified red mud (AMRM) catalyst to isomerize the trans-2-butene and cis-2-butene to form 1-butene, and a product purification system to isolate the 1-butene product stream from an effluent from the reactor.

In an aspect, the butene feedstock has a boiling point range of about −20° C. to about 10° C. In an aspect, the product purification system includes a distillation column configured to recycle the effluent to the upstream purification system, after removal of the 1-butene product stream.

Other implementations are also within the scope of the following claims.

What is claimed is:

1. A method for using an acid modified red mud (AMRM) catalyst for olefin isomerization, comprising:
    forming the AMRM catalyst by:
        dissolving red mud in water to form a red mud solution;
        neutralizing the red mud solution with an acid;
        forming a precipitant by adding a base to the neutralized red mud solution;
        filtering the precipitant from the red mud solution containing the added base;
        drying the precipitant;
        grinding the dried precipitant to form particles of less than 100 μm; and
        calcining the particles to form the AMRM catalyst; and
    flowing a butene feedstock comprising 2-butene over the AMRM catalyst in an isomerization reactor to obtain a reactor effluent comprising 1-butene; and
    separating 1-butene from the reactor effluent.

2. The method of claim 1, further comprising calcining the AMRM catalyst to activate the AMRM catalyst at a temperature of between about 400° C. and about 700° C. for between about 2 hours and about 6 hours.

3. The method of claim 1, further comprising calcining the AMRM catalyst to activate the AMRM catalyst at a temperature of between about 500° C. and about 600° C. for between about 3 hours and about 5 hours.

4. The method of claim 1, further comprising calcining the AMRM catalyst to activate the AMRM catalyst at a temperature of about 550° C. for about 4 hours.

5. The method of claim 1, further comprising obtaining the butene feedstock from an upstream purification system in a refinery.

6. The method of claim 1, comprising obtaining the butene feedstock with a boiling point range of between about −30° C. and about 40° C.

7. The method of claim 1, comprising obtaining the butene feedstock with a boiling point range of between about −20° C. and about 10° C.

8. The method of claim 1, comprising obtaining the butene feedstock with a boiling point range of between about −10° C. and about 0° C.

9. The method of claim 1, further comprising flowing the butene feedstock over the AMRM catalyst at a weight hour space velocity of between about 400 hr$^{-1}$ and 1300 hr$^{-1}$.

10. The method of claim 1, further comprising flowing the butene feedstock over the AMRM catalyst at a weight hour space velocity of between about 650 hr$^{-1}$ and 1150 hr$^{-1}$.

11. The method of claim 1, further comprising flowing the butene feedstock over the AMRM catalyst at a weight hour space velocity of about 900 hr$^{-1}$.

12. The method of claim 1, further comprising separating the 1-butene from the reactor effluent in a distillation column.

13. The method of claim 1, further comprising returning the reactor effluent to an upstream purification system after removal of the 1-butene from the reactor effluent.

14. The method of claim 1, further comprising combining the reactor effluent with the butene feedstock after separating the 1-butene from the reactor effluent.

* * * * *